(12) United States Patent
Chen et al.

(10) Patent No.: US 11,559,705 B2
(45) Date of Patent: Jan. 24, 2023

(54) NEUTRON CAPTURE THERAPY SYSTEM (71) Applicant: NEUBORON MEDTECH LTD., Jiangsu (CN)

(72) Inventors: Wei-Lin Chen, Jiangsu (CN); Yuan-Hao Liu, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 754 days.

(21) Appl. No.: 16/511,142

(22) Filed: Jul. 15, 2019

(65) Prior Publication Data
US 2019/0351257 A1   Nov. 21, 2019

Related U.S. Application Data

(63) Continuation of application No. PCT/CN2017/092725, filed on Jul. 13, 2017.

(30) Foreign Application Priority Data

Jun. 5, 2017  (CN) .......................... 201710413549.7
Jun. 5, 2017  (CN) .......................... 201720641461.6

(51) Int. Cl.
*A61N 5/10*   (2006.01)
*A61K 41/00*   (2020.01)
(Continued)

(52) U.S. Cl.
CPC ........ *A61N 5/1077* (2013.01); *A61K 41/0095* (2013.01); *G21K 1/10* (2013.01);
(Continued)

(58) Field of Classification Search
CPC .......... A61N 5/1077; A61N 2005/1087; A61N 2005/109; A61N 2005/1095; A61N 5/10; A61K 41/0095; G21K 1/10; G21K 1/02
See application file for complete search history.

(56) References Cited

U.S. PATENT DOCUMENTS 4,157,475 A * 6/1979 Stock ................. A61N 5/10
                                             976/DIG. 428
4,359,642 A * 11/1982 Heinz ................. G21K 1/02
                                             976/DIG. 428
(Continued)

FOREIGN PATENT DOCUMENTS

CN       101896226 A      11/2010
CN       104053476 B      11/2015
(Continued)

OTHER PUBLICATIONS

International Search Report of PCT/CN2017/092725, dated Feb. 26, 2018.

*Primary Examiner* — David A Vanore
(74) *Attorney, Agent, or Firm* — Locke Lord LLP; Tim Tingkang Xia, Esq.

(57) ABSTRACT

A beam shaping assembly (10) used in a neutron capture system and capable of changing an irradiation range of a neutron beam. The beam shaping assembly includes: a beam inlet (11), a target (12), a moderator (13) adjoining the target (12), a reflector (14) surrounding the moderator (13), a thermal neutron absorber (15) adjoining the moderator (13), a radiation shield (16) arranged inside the beam shaping assembly (10), and a beam outlet (17). The beam shaping assembly (10) further includes replacement components (21, 22) that can be attached to and detached from the beam shaping assembly (10) to change the irradiation range of the neutron beam.

18 Claims, 4 Drawing Sheets

(51) Int. Cl.
*G21K 1/10* (2006.01)
*G21K 1/02* (2006.01)

(52) U.S. Cl.
CPC ... *A61N 2005/109* (2013.01); *A61N 2005/1087* (2013.01); *G21K 1/02* (2013.01)

(56) References Cited

U.S. PATENT DOCUMENTS

| | | | | |
|---|---|---|---|---|
| 2015/0083935 A1* | 3/2015 | Latham | ............ | G21K 5/04 |
| | | | | 250/492.3 |
| 2016/0082282 A1* | 3/2016 | Kumada | ............ | C04B 35/64 |
| | | | | 252/478 |
| 2016/0158579 A1* | 6/2016 | Liu | ............ | H05H 3/06 |
| | | | | 600/1 |
| 2016/0351282 A1* | 12/2016 | Kumada | ............ | C04B 35/645 |
| 2016/0366385 A1* | 12/2016 | Chappelow | ............ | H04N 9/735 |
| 2017/0062087 A1* | 3/2017 | Abbasi | ............ | A61N 5/1042 |
| 2019/0351257 A1* | 11/2019 | Chen | ............ | A61K 41/0095 |
| 2020/0282238 A1* | 9/2020 | Liu | ............ | G21G 4/02 |
| 2021/0060360 A1* | 3/2021 | Liu | ............ | C04B 41/84 |
| 2022/0080224 A1* | 3/2022 | Chen | ............ | A61N 5/1065 |

FOREIGN PATENT DOCUMENTS

| | | |
|---|---|---|
| CN | 106310540 A | 1/2017 |
| EP | 2532385 A1 | 12/2012 |
| EP | 2805745 A1 | 11/2014 |
| EP | 2874473 A1 | 5/2015 |
| EP | 3032926 A1 | 6/2016 |
| GB | 1409263 A | 10/1975 |
| JP | 1974001997 A | 1/1974 |
| JP | 2007242422 A | 9/2007 |
| JP | 2008022920 A | 2/2008 |
| JP | 2016107047 A | 6/2016 |
| JP | 2018161449 A | 10/2018 |
| RU | 2252798 C2 | 5/2005 |

\* cited by examiner

NEUTRON CAPTURE THERAPY SYSTEM

CROSS-REFERENCE TO RELATED PATENT APPLICATION

This application is a continuation application of International Application No. PCT/CN2017/092725, filed on Jul. 13, 2017, which claims priority to Chinese Patent Application No. 201710413549.7, filed on Jun. 5, 2017 and Chinese Patent Application No. 201720641461.6, filed on Jun. 5, 2017, the disclosures of which are hereby incorporated by reference.

FIELD

The present disclosure relates generally to a beam shaping assembly, and, more particularly, to a beam shaping assembly for neutron capture therapy

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastomamultiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Figure 1:
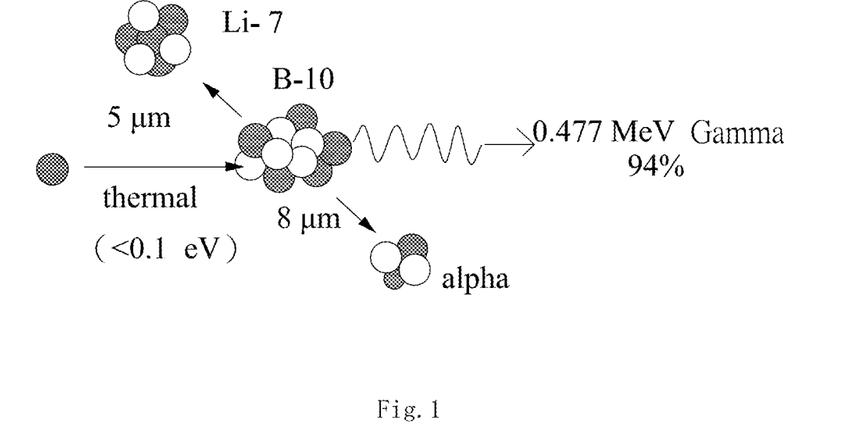
FIG. 1 is a schematic view of boron neutron capture reaction.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. As illustrated in FIG. 1, a schematic view of boron neutron capture reaction are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

BNCT is also well known for binary cancer therapy, for its effectiveness depending on the concentration of the boronated pharmaceuticals and the number of the thermal neutrons at the tumor site. The beam shaping assembly in the existing accelerator based boron neutron capture therapy (AB-BNCT) facility usually adopts a variety of collimators with different apertures to adjust the neutron beam. However, in the absence of a collimator, the beam outlet is made up of a reflector and a neutron shield, so the variable range of the beam outlet is limited by relying solely on the collimator's confinement of the beam outlet. For example, when the beam outlet radius of the beam shaping assembly without the collimator is 7 cm, and the tumor area is large, the tumor area cannot be completely irradiated due to the small beam irradiation range. When the beam outlet radius of the beam shaping assembly without the collimator is 10 cm and the tumor area is small, even if a collimator is added, the collimator is limited by its thickness, and because the beam irradiation range is too large, the beam irradiation area cannot be effectively limited, resulting in unnecessary irradiation of surrounding normal tissues.

Therefore, it is really necessary to provide a new technical solution so as to solve the foregoing problem.

SUMMARY

In order to provide a beam shaping assembly capable of changing the irradiation range of the neutron beam, an aspect of the present disclosure provides a beam shaping assembly for neutron capture therapy includes a beam inlet; a target for generating a nuclear reaction with a proton beam incident from the beam inlet to generate neutrons that forms a neutron beam which defines a main axis; a moderator adjacent to the target for decelerating the neutrons generated by the target to an epithermal neutron energy region; a reflector surrounding the moderator for leading the neutrons deflected from the main axis back to the main axis to converge the epithermal neutrons; a thermal neutron absorber adjacent to the moderator for absorbing thermal neutrons to avoid excessive dose to superficial normal tissue during treatment; a radiation shield for shielding leaking neutrons and photons to reduce dose to normal tissue in non-irradiated area; and a replacement device forming a beam outlet, wherein the replacement device is detachable from the beam shaping assembly to change an irradiation range of the neutron beam.

Further, the replacement device includes a first replacement member including a first end having a first diameter away from the target and a second end having a second diameter close to the target and a second replacement member including a third end having a third diameter away from the target and a fourth end having a fourth diameter close to the target, the first end of the first replacement member forms a beam outlet having a first aperture, the third end of the second replacement member forms a beam outlet having a second aperture, and the first aperture is not equal to the second aperture.

Further, the first replacement member has a main body connecting the first end and the second end, and an outer surface of the main body is parallel to the main axis, it can be understood that the outer surface of the main body is cylindrical.

More particularly, the first replacement member has a main body connecting the first end and the second end, and an outer surface of the main body is inclined from the first end toward the second end to form a tapered structure having a gradually decreasing diameter, it can be understood that the main body is tapered, and an inner surface of the main body is inclined from the second end toward the first end to form a tapered structure having a gradually decreasing diameter.

In other embodiment, the first replacement member has a main body connecting the first end and the second end, and an outer surface of the main body is inclined from the second end toward the first end to form a tapered structure having a gradually decreasing diameter, and an inner surface of the main body is inclined from the second end toward the first end to form a tapered structure having a gradually decreasing diameter. In this embodiment, since the second diameter of the second end is larger than the first diameter of the first end, it is hardly for the integrated first replacement member to be mounted into the beam shaping assembly, as a way to solve this problem, the first replacement member is divided into several sub replacement members along the circumferential direction, and the sub replacement members are mounted into the beam shaping assembly one by one to limit the irradiation range of the beam outlet.

Further, the first end is provided with a through hole extending therethrough to the second end, the through hole forms the beam outlet on the first end, and the neutron beam irradiates from the beam outlet.

Further, the beam shaping assembly has an inner surface, the radiation shield has an end portion, and the first replacement member has a main body connecting a first end and a second end, the first replacement member is mounted in the beam shaping assembly from the end portion, an outer surface of the main body is in contact with the inner surface of the beam shaping assembly, and the first end is flush with the end portion or protrudes from the end portion in a direction away from the target.

More particularly, the first replacement member is disposed on the front side of the moderator along the incident direction of the proton beam and is flush with the end portion or protrudes from the end portion in a direction away from the target, and the first replacement member is part of reflector and/or part of radiation shield.

Further, the moderator includes two mutually adjacent tapered portions, one of which is adjacent to the beam inlet and the other of which is adjacent to the beam outlet, and the first replacement member is adjacent to a rear side of the tapered portion of the moderator near the beam outlet.

Further, the reflector is made of any one or more of Pb or Ni, and the radiation shield includes a photon shield made of Pb and a neutron shield made of polyethylene.

Particularly, the beam shaping assembly is further provided for accelerator-based boron neutron capture therapy which accelerates the proton beam by an accelerator, the target is made of a metal, the proton beam is accelerated to an energy sufficient to overcome the coulomb repulsion of the target nucleus and undergo a nuclear reaction with the target to produce neutrons, the beam shaping assembly can slow the neutron to the epithermal neutron energy region and reduce contents of thermal neutrons and fast neutrons, the epithermal neutron energy region is between 0.5 eV and 40 keV, the thermal neutron energy region is smaller than 0.5 eV, and the fast neutron energy region is greater than 40 keV.

In order to provide a beam shaping assembly capable of changing the irradiation range of the neutron beam, another aspect of the present disclosure provides a beam shaping assembly for neutron capture therapy includes a beam inlet; a target for generating a neutron beam after being irradiated by an incident charged particle beam from the beam inlet; a moderator adjacent to the target for decelerating the neutrons generated by the target to an epithermal neutron energy region; a reflector surrounding the moderator for leading the deflected neutrons back to converge epithermal neutrons; a thermal neutron absorber adjacent to the moderator for absorbing thermal neutrons to avoid excessive dose to superficial normal tissue during treatment; a radiation shield for shielding leaking neutrons and photons to reduce dose to normal tissue in non-irradiated area; and a beam outlet, wherein the beam outlet is changeable to change an irradiation range of the neutron beam.

Further, the irradiation range of the beam outlet is changed by mounting a replacement device into the beam shaping assembly or detaching the replacement device from the beam shaping assembly.

Further, the replacement device includes a replacement member, the replacement member includes a first end, a second end and a main body connecting the first end and the second end, a first aperture is disposed on the first end, a second aperture is disposed on the second end and connected to the first aperture, the replacement device is mounted into the beam shaping assembly from the beam outlet, the second end is adjacent to the target, and the first end is flush with or protrudes from the beam outlet, the first aperture on the first end limits the irradiation range of the beam outlet.

For different replacement member has different diameter of the first aperture, mount the replacement member with proper diameter into the beam shaping assembly according to the actual therapy requirement.

Particularly, the beam shaping assembly has an inner surface between the moderator and the beam outlet, the main body has an outer surface, and the outer surface is contacted to the inner surface.

In order to provide a beam shaping assembly capable of changing the irradiation range of the neutron beam, another aspect of the present disclosure provides a beam shaping assembly for neutron capture therapy includes a beam inlet; a target for generating a neutron beam after being irradiated by an incident charged particle beam from the beam inlet; a moderator adjacent to the target for decelerating the neutrons generated by the target to an epithermal neutron energy region; a reflector surrounding the moderator for leading the deflected neutrons back to converge epithermal neutrons; a thermal neutron absorber adjacent to the moderator for absorbing thermal neutrons to avoid excessive dose to superficial normal tissue during treatment; a radiation shield for shielding leaking neutrons and photons to reduce dose to normal tissue in non-irradiated area; a first beam outlet forming a first irradiation range; and a second beam outlet forming a second irradiation range different from the first irradiation range.

Further, part of the reflector or/and part of the radiation shield are moveable to be mounted into or detached from the beam shaping assembly to decrease or enlarge the irradiation range of the first beam outlet or the second beam outlet.

Further, a movable part of the reflector and the radiation shield form a first replacement member with a first aperture.

Further, a gap channel is provided between the moderator and the reflector to increase the epithermal neutron flux.

Particularly, the first replacement member is mounted into the beam shaping assembly, the first replacement member includes a first end, a second end and an inner surface extending form the first end to the second end, the first aperture is disposed on the first end flush with or protrudes from the beam outlet, the second end is adjacent to the gap channel, and the inner surface of the first replacement member is communicated with the gap channel.

The term 'cylindrical structure' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

The term 'tapered structure' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

Compared to the prior art, the beam shaping assembly for neutron capture therapy changes its irradiation range of the beam outlet by mounting or detaching the replacement device, so as to achieve an appropriate irradiation range of the beam shaping assembly during the real irradiation therapy.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^{7}Li$ (p, n) $^{7}Be$ and $^{9}Be$ (p, n) $^{9}B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, and high temperature resistance etc. But in reality, no nuclear reactions may satisfy all requests, in the present disclosure, the target is made of lithium. And it is known to those skilled in art, besides the referred metal materials, the target can also be made of other metal materials.

Requirements for the heat removal system differ as the selected nuclear reactions. $^{7}Li$ (p, n) $^{7}Be$ asks for more than $^{9}Be$ (p, n) $^{9}B$ does because of low melting point and poor thermal conductivity coefficient of the metal (lithium) target. In these embodiments of the present disclosure is $^{7}Li$ (p, n) $^{7}Be$.

No matter BNCT neutron sources are from the nuclear reactor or the nuclear reactions between the accelerator charged particles and the target, only mixed radiation fields are produced, that is, beams include neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux>$1\times10^{9}$ n/cm$^{2}$ s
Fast neutron contamination<$2\times10^{-13}$ Gy-cm$^{2}$/n
Photon contamination<$2\times10^{-13}$ Gy-cm$^{2}$/n Thermal to epithermal neutron flux ratio<0.05

Epithermal neutron current to flux ratio>0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time<=30 min (proton current for accelerator is 10 mA)

2. 30.0 RBE-Gy treatable depth>=7 cm

3. The maximum tumor dose>=60.0 RBE-Gy

4. The maximum dose of normal brain tissue<=12.5 RBE-Gy

5. The maximum skin dose<=11.0 RBE-Gy

Note: RBE stands for relative biological effectiveness. Since photons and neutrons express different biological effectiveness, the dose above should be multiplied with RBE of different tissues to obtain equivalent dose.

In actual neutron capture therapy process, the irradiation range of the neutron beam is also an important factor that should be considered. Embodiments of the present disclosure are directed to improvements in beam shaping assembly for neutron capture therapy, and in certain embodiment, it is an improvement for beam shaping assembly for accelerator based boron neutron capture therapy.

Figure 3:
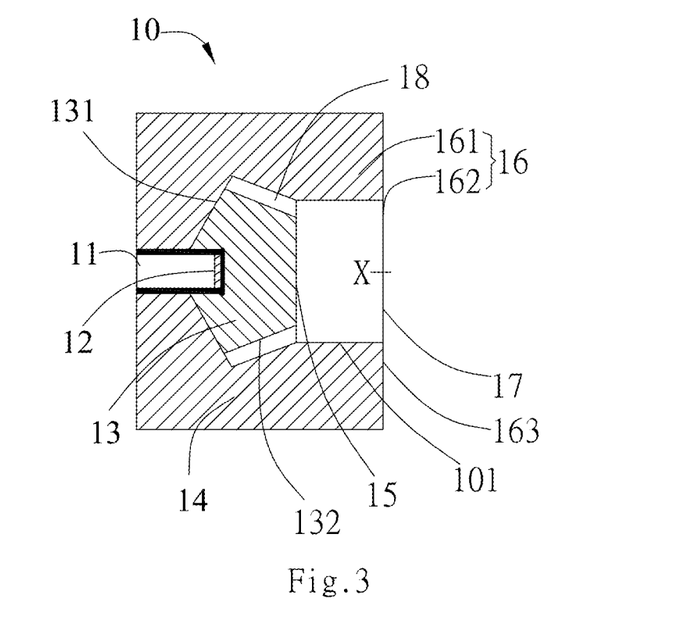
FIG. 3 is a plain view of a beam shaping assembly in which no replacement device is mounted in the present application.

As shown in FIG. 3, the beam shaping assembly 10 includes a beam inlet 11, a target 12, a moderator 13 adjacent to the target 12, a reflector 14 surrounding the moderator 13, a thermal neutron absorber 15 adjacent to the moderator 13, a radiation shield 16 and a beam outlet 17 disposed within the beam shaping assembly 10, the target 12 has a nuclear reaction with a proton beam incident from the beam inlet 11 to produce neutrons and forms a neutron beam which defines a main axis X, the moderator 13 decelerates neutrons generated from the target 12 to an epithermal neutron energy region, and the reflector 14 directs neutrons deviating from the main axis X back to converge the epithermal neutrons, a gap passage 18 is provided between the moderator 13 and the reflector 14 to increase the epithermal neutron flux, the thermal neutron absorber 15 is provided for absorbing thermal neutrons to avoid excessive dose to superficial normal tissue during treatment, the radiation shield 16 is provided for shielding leaking neutrons and photons to reduce dose to normal tissue in non-irradiated area.

In the process of boron neutron capture therapy, in order to achieve better therapeutic effects and reduce damage to healthy tissues, it is necessary to provide different neutron beam irradiation ranges for different sizes of tumors, therefore it is desirable to provide a beam shaping assembly 10 that is capable of adjusting the neutron beam irradiation range. In the present disclosure, the adjustment of the neutron beam irradiation range is achieved by providing a replacement device 20. The beam shaping assembly 10 further includes a replacement device 20 including a first replacement member 21 and a second replacement member 22 with different sizes. The first replacement member 21 and the second replacement member 22 can be mounted in the beam shaping assembly 10, respectively, and can be removed from the beam shaping assembly 10 to be replaced with each other.

Figure 2:
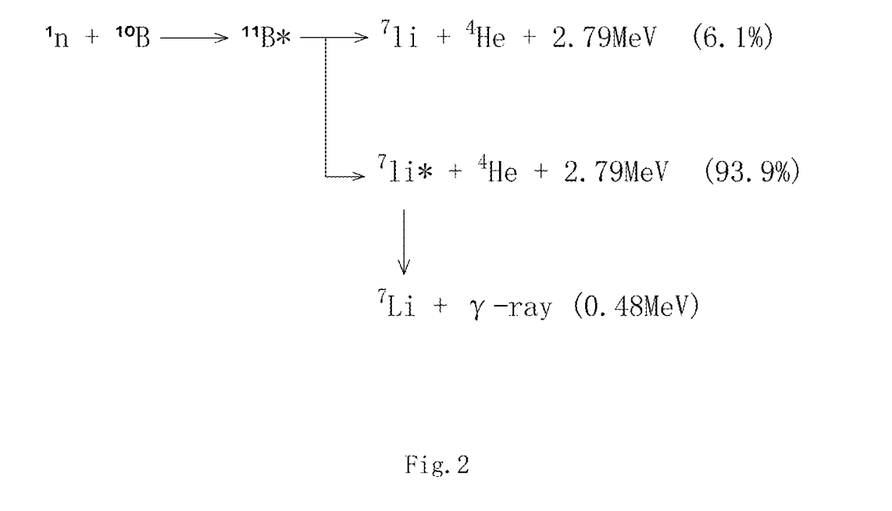
FIG. 2 is a nuclear reaction formula of $^{10}B(n,\alpha)^{7}Li$ neutron capture.

The accelerator based boron neutron capture therapy accelerates the proton beam by an accelerator. In certain embodiment, the target 12 is made of lithium metal, the proton beam is accelerated to an energy sufficient to overcome the coulomb repulsion of the target nucleus, and undergoes $^7$Li(p,n)$^7$Be nuclear reaction with the target 12 to produce neutrons (as shown in FIG. 1 and FIG. 2). The beam shaping assembly 10 decelerates the neutrons to the epithermal neutron energy region and reduce the contents of thermal neutrons and fast neutrons. The moderator 13 is made of a material having a large action cross section with fast neutron and a small action cross section with superheated neutron, as in certain embodiment, the moderator 13 is made of any one or more of $D_2O$, $AlF_3$, Fluental™, $CaF_2$, $Li_2CO_3$, $MgF_2$ and $Al_2O_3$. The reflector 14 is made of a material having a strong neutron reflection ability, and as in certain embodiments, the reflector 14 is made of any one or more of Pb or Ni. The thermal neutron absorber 15 is made of a material having a large action cross section with thermal neutrons, and as in certain embodiments, the thermal neutron absorber 15 is made of $^6$Li. An air passage 19 is provided between the thermal neutron absorber 15 and the beam outlet 17, and the arrangement of the air passages 19 continually direct neutrons deviating from the main axis back to achieve an effect of converging epithermal neutrons. The radiation shield 16 includes a photon shield 161 and a neutron shield 162. As in certain embodiments, the photon shield 161 is made of lead (Pb) and the neutron shield 162 is made of polyethylene (PE).

The moderator 13 is disposed as two tapered portions that are adjacent to each other in opposite directions. In the direction shown in FIG. 3, the left side of the moderator 13 is a tapered portion 131 which gradually becomes smaller toward the left side, the right side of the moderator 13 is a tapered portion 132 which gradually becomes smaller toward the right side, and the two tapered portions are adjacent to each other. The tapered portion 131 on the left side of the moderator 13 is a tapered portion near the beam inlet 11, and the tapered portion 132 on the right side of the moderator 13 is a tapered portion close to the beam outlet 17. The moderator 13 is surrounded by the reflector 14, and a gap passage 18 is provided between the moderator 13 and the reflector 14. The so-called gap passage 18 refers to an empty region that is not covered by a solid material and where the neutron beam is easily passed, the gap passage 18 maybe an air channel or a vacuum channel. The thermal neutron absorber 15 disposed adjacent to the moderator 13 is made of a very thin layer of $^6$Li material, and the photon shield 161 made of Pb may be provided integrally or separately with the reflector 14. The neutron shield 162 made of PE maybe disposed adjacent to the beam outlet 17. As is well known to those skilled in the art, the photon shield 161 maybe made of other materials as long as it functions to shield photons, and the neutron shield 162 may also be made of other materials as long as the shielding capability of the materials for shielding the leaking neutrons is enough.

Figure 4:
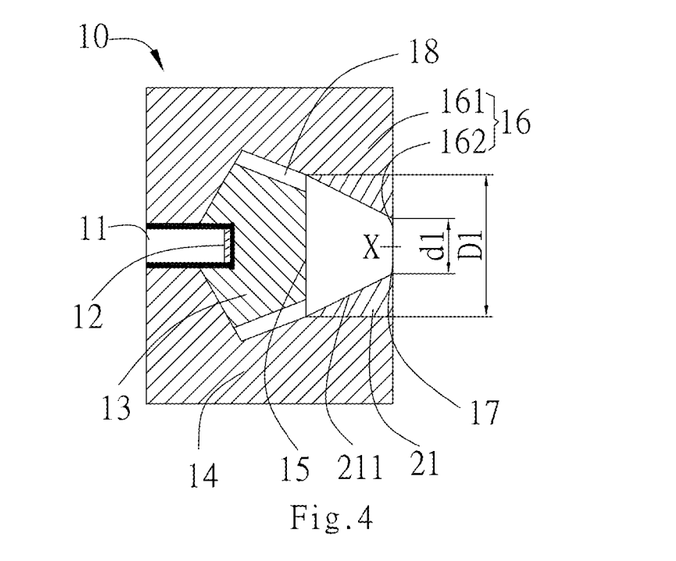
FIG. 4 is a plain cross-sectional view of a beam shaping assembly provided with a first replacement member.
Figure 5:
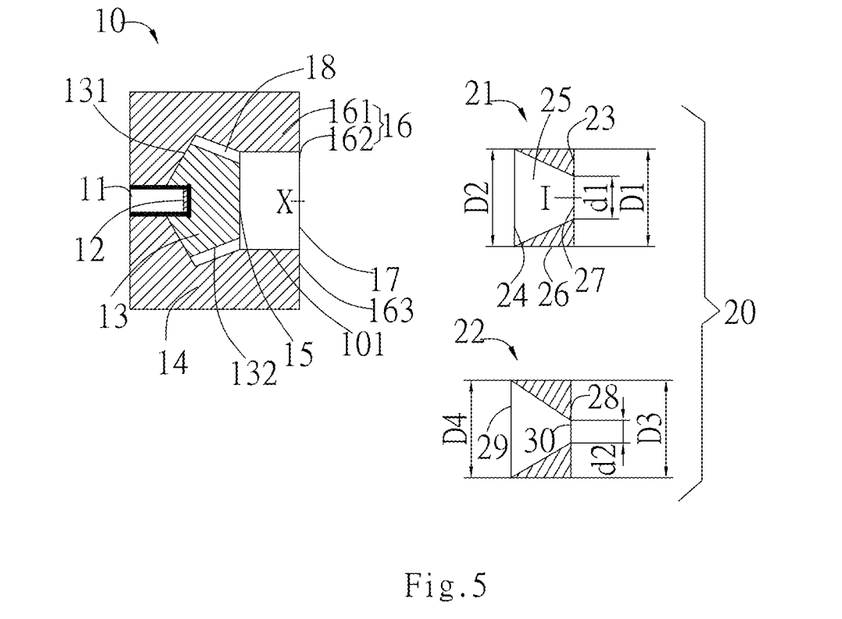
FIG. 5 is a schematic view of the first replacement member being mounted to the beam shaping assembly and the second replacement member not being mounted in the beam shaping assembly.

Referring to FIGS. 4 and 5, the radiation shield 16 has an end portion 163 located at the outermost side of the beam shaping assembly 10 and closest to the object to be irradiated, and the beam shaping assembly 10 has an inner surface 101. The first replacement member 21 is mounted from the end portion 163 of the radiation shield 16 into the beam shaping assembly 10 and is located on the rear side of the tapered portion 132 of the moderator 13 near the end portion 163 of the radiation shield 16 (i.e., the first replacement member 21 is disposed on the front side of the moderator 13 along the incident direction of the proton beam), and the outer surface 26 of the first replacement member 21 is in contact with the inner surface 101 of the beam shaping assembly 10. In order to facilitate the mounting of the first replacement member 21 in the beam shaping assembly 10, the first replacement member 21 can be detached from the beam shaping assembly 10 to be replaced with the second replacement member 22, the structure of the first replacement member 21 is designed as follows.

Figure 6A:
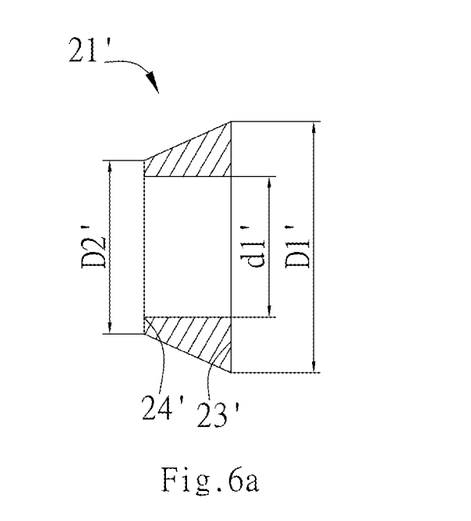
FIG. 6a is a schematic view of another embodiment of the first replacement member in FIG. 5.

The first replacement member 21 has a first end 23, a second end 24, and a main body 25 connecting the first end 23 and the second end 24. The inner surface 211 of the first replacement member 21 is inclined from the second end 24 toward the first end 23 to form a tapered structure having a gradually decreasing diameter. The first end 23 is away from the target 12 and is flush with the end portion 163 of the radiation shield 16 or protrudes from the end portion 163 in a direction away from the target 12. The second end 24 is adjacent to the target 12, and the diameter D1 of the first end 23 is not less than the diameter D2 of the second end 24. As certain embodiment, the outer surface 26 of the main body 25 is parallel to the main axis X defined by the neutron beam, i.e., the outer surface 26 of the main body 25 has a cylindrical structure. The first end 23 is provided with a through hole 27 extending therethrough to the second end 24, and the through hole 27 forms a beam outlet with a first aperture d1 on the first end 23. As another embodiment, the outer surface of the main body 25' may be disposed to be inclined from the first end 23' toward the second end 24' to form a tapered structure having a gradually decreasing diameter. Referring to FIG. 6a, the diameter D1' of the first end 23' is greater than the diameter D2' of the second end 24', and the first end 23' of the first replacement member 21' forms a beam outlet having a first aperture d1'.

Figure 6B:
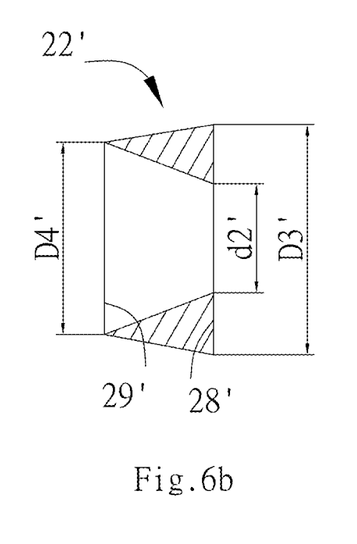
FIG. 6b is a schematic view of another embodiment of the second replacement member in FIG. 5, wherein the second replacement member has a smaller diameter than the diameter of the beam outlet and the main body of the replacement member is a tapered portion.

The second replacement member 22 has a third end 28 and a fourth end 29, and the diameter D3 of the third end 28 is not less than the diameter D4 of the fourth end 29. The third end 28 is forwardly provided with a through hole 30 extending therethrough to the fourth end 29, and the through hole 30 forms the beam outlet with a second diameter d2 on the third end 28. In order to ensure the interchangeability of the second replacement member 22 with the first replacement member 21 while achieving the effect of adjusting the irradiation range of the neutron beam, in certain embodiment, the structure of the second replacement member 22 is referred to the structure of the first replacement member 21 such that the dimensions of the first aperture d1 and the second aperture d2 do not coincide. FIG. 6b shows that the outer surface of the second replacement member 22' is disposed to be inclined from the first end 28' toward the second end 29' to form a tapered structure having a gradually decreasing diameter, the diameter D3' of the third end 28' is greater than the diameter D4' of the second end 29', and the third end 28' of the second replacement member 22' forms a beam outlet having a second aperture d2'.

For example, the first replacement member 21 is mounted in the beam shaping assembly 10, when the first aperture d1 formed by the through hole 27 of the first replacement member 21 on the first end 23 is small, while the irradiation range of the neutron beam needs to be irradiated is large in actual irradiation therapy, remove the first replacement member 21 from the beam shaping assembly 10, and mount the second replacement member 22 with the second aperture having a larger diameter d2 formed on the third end 23. Similarly, when the first aperture d1 formed by the through hole 27 of the mounted first replacement member 21 on the first end 23 is large, while the irradiation range of the neutron beam needs to irradiates is small in actual irradiation therapy, remove the first replacement member 21 from the beam shaping assembly 10, and mount the second replacement member 22 with the second aperture having a smaller diameter d2 formed on the third end 23. The first replacement member and the second replacement member have a wide variety of configurations and sizes, and a first replacement member or a second replacement member having a suitable beam outlet diameter may be selected according to the specific needs of the irradiation range of the neutron beam.

The replacement device 20 is capable of directing the neutrons deviating from the main axis X back to achieve the effect of converging the epithermal neutrons, as well as shielding the leaking neutrons or/and photons. In certain embodiments, in the present disclosure, the replacement device 20 is part of the reflector 14 and the radiation shield 16, it can be understood that the replacement device 20 is an integrated structure consists of part of the reflector 14 and part of the radiation shield 16. The first replacement member 21 is mounted in the beam shaping assembly 10 to converge the neutron beam, replace the first replacement member 21 with the second replacement member 21 with a suitable diameter of the second aperture according to actual needs to adjust the irradiation range of the neutron beam. Certainly, the replacement device 20 is not limited to include part of reflector 14 and/or part of radiation shield 16, but may also include part of the moderator 13 and/or part of thermal neutron absorber 15, the replacement device 20 may include part of the collimator (not shown). When the first end of the first replacement member protrudes from the end portion 163 in a direction away from the target 12, it can be understood that the first replacement member 21 includes part of the collimator, as long as the aperture of the beam outlet can be adjusted to change the irradiation range of the neutron beam by the arrangement of the device 20 and achieve the effect of converging thermal neutrons to different extents.

In the present disclosure, the replacement device 20 may include only one replacement member. When the first replacement member is not mounted as show in FIG. 5, a beam outlet with a large aperture may be formed. After the first replacement member is mounted, a relatively small aperture beam outlet is formed. The replacement device 20 may also include a first replacement member 21 and a second replacement member 22 or more replacement members to form different sizes of aperture of beam outlets.

The term 'cylindrical structure' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

The term 'tapered structure' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A beam shaping assembly for neutron capture therapy comprising:
   a beam inlet;
   a target for generating a nuclear reaction with a proton beam incident from the beam inlet to generate neutrons that forms a neutron beam, wherein the neutron beam defines a main axis;
   a moderator adjacent to the target for decelerating the neutrons generated by the target to an epithermal neutron energy region;
   a reflector surrounding the moderator for leading the neutrons deflected from the main axis back to the main axis to converge epithermal neutrons;
   a thermal neutron absorber adjacent to the moderator for absorbing thermal neutrons to avoid excessive dose to superficial normal tissue during treatment;
   a radiation shield for shielding leaking neutrons and photons to reduce dose to normal tissue in non-irradiated area; and
   a beam outlet, wherein the beam outlet is changeable to change an irradiation range of the neutron beam.

2. The beam shaping assembly for neutron capture therapy according to claim 1, wherein the beam outlet is formed by a replacement device, the replacement device is detachable from the beam shaping assembly, and the replacement device comprises:
   a first replacement member comprising a first end having a first diameter away from the target and a second end having a second diameter close to the target; and
   a second replacement member comprising a third end having a third diameter away from the target and a fourth end having a fourth diameter close to the target,
   wherein the first end of the first replacement member forms a beam outlet having a first aperture, the third end of the second replacement member forms a beam outlet having a second aperture, and the first aperture is not equal to the second aperture.

3. The beam shaping assembly for neutron capture therapy according to claim 2, wherein the first replacement member has a main body connecting the first end and the second end, and an outer surface of the main body is parallel to the main axis.

4. The beam shaping assembly for neutron capture therapy according to claim 2, wherein the first replacement member has a main body connecting the first end and the second end, and an outer surface of the main body is inclined from the first end toward the second end to form a tapered structure having a gradually decreasing diameter, and an inner surface of the main body is inclined from the second end toward the first end to form a tapered structure having a gradually decreasing diameter.

5. The beam shaping assembly for neutron capture therapy according to claim 2, wherein the first end is provided with a through hole extending therethrough to the second end, the through hole forms the beam outlet on the first end, and the neutron beam irradiates from the beam outlet.

6. The beam shaping assembly for neutron capture therapy according to claim 2, wherein the beam shaping assembly has an inner surface, the radiation shield has an end portion, and the first replacement member has a main body connecting a first end and a second end, the first replacement member is mounted in the beam shaping assembly from the end portion, an outer surface of the main body is in contact with the inner surface of the beam shaping assembly, and the first end is flush with the end portion or protrudes from the end portion in a direction away from the target.

7. The beam shaping assembly for neutron capture therapy according to claim 6, wherein the first replacement member is disposed on the front side of the moderator along the incident direction of the proton beam and is flush with the end portion or protrudes from the end portion in a direction away from the target, and the first replacement member is part of reflector and/or part of radiation shield.

8. The beam shaping assembly for neutron capture therapy according to claim 7, wherein the moderator comprises two mutually adjacent tapered portions, one of which is adjacent to the beam inlet and the other of which is adjacent to the beam outlet, and the first replacement member is adjacent to a rear side of the tapered portion of the moderator near the beam outlet.

9. The beam shaping assembly for neutron capture therapy according to claim 1, wherein the reflector is made of any one or more of Pb or Ni, and the radiation shield comprises a photon shield made of Pb and a neutron shield made of polyethylene.

10. A method for performing accelerator-based boron neutron capture therapy, comprising:
providing the beam shaping assembly for neutron capture therapy according to claim 1; and
accelerating the proton beam by an accelerator,
wherein the target is made of a metal, the proton beam is accelerated to an energy sufficient to overcome the coulomb repulsion of the target nucleus and undergo a nuclear reaction with the target to produce neutrons, the beam shaping assembly moderates neutrons to the epithermal neutron energy region and reduces contents of thermal neutrons and fast neutrons, the epithermal neutron energy region is between 0.5 eV and 40 keV, the thermal neutron energy region is smaller than 0.5 eV, and the fast neutron energy region is greater than 40 keV.

11. A beam shaping assembly for neutron capture therapy comprising:
a beam inlet;
a target for generating a neutron beam after being irradiated by an incident charged particle beam from the beam inlet;
a moderator adjacent to the target for decelerating the neutrons generated by the target to an epithermal neutron energy region;
a reflector surrounding the moderator for leading the neutrons being deflected back to converge epithermal neutrons;
a thermal neutron absorber adjacent to the moderator for absorbing thermal neutrons to avoid excessive dose to superficial normal tissue during treatment;
a radiation shield for shielding leaking neutrons and photons to reduce dose to normal tissue in non-irradiated area; and
a beam outlet, wherein the beam outlet is changeable to change an irradiation range of the neutron beam;
wherein the beam shaping assembly has an inner surface between the moderator and the beam outlet, the main body has an outer surface, and the outer surface is contacted to the inner surface.

12. The beam shaping assembly for neutron capture therapy according to claim 11, further comprising a replacement device configured to be detachably mounted into the beam shaping assembly from the beam outlet to change an irradiation range of the neutron beam, wherein the irradiation range of the beam outlet is changed by mounting the replacement device into the beam shaping assembly or detaching the replacement device from the beam shaping assembly, the replacement device comprises a replacement member, the replacement member comprises a first end, a second end and a main body connecting the first end and the second end, a first aperture is disposed on the first end, a second aperture is disposed on the second end and connected to the first aperture, the replacement device is mounted into the beam shaping assembly from the beam outlet, the second end is adjacent to the target, and the first end is flush with or protrudes from the beam outlet, the first aperture on the first end limits the irradiation range of the beam outlet.

13. The beam shaping assembly for neutron capture therapy according to claim 12, wherein the replacement device comprises a plurality of replacement members, and different replacement members has different diameters of the first aperture.

14. A beam shaping assembly for neutron capture therapy comprising:
a beam inlet;
a target for generating a neutron beam after being irradiated by an incident charged particle beam from the beam inlet;
a moderator adjacent to the target for decelerating the neutrons generated by the target to an epithermal neutron energy region;
a reflector surrounding the moderator for leading the neutrons being deflected back to converge epithermal neutrons;
a thermal neutron absorber adjacent to the moderator for absorbing thermal neutrons to avoid excessive dose to superficial normal tissue during treatment;
a radiation shield for shielding leaking neutrons and photons to reduce dose to normal tissue in non-irradiated area;
a first beam outlet forming a first irradiation range; and
a second beam outlet forming a second irradiation range different from the first irradiation range.

15. The beam shaping assembly for neutron capture therapy according to claim 14, wherein part of the reflector or/and part of the radiation shield are moveable to be mounted into or detached from the beam shaping assembly to decrease or enlarge the irradiation range of the first beam outlet or the second beam outlet.

16. The beam shaping assembly for neutron capture therapy according to claim 15, wherein a movable part of the reflector and the radiation shield form a first replacement member with a first aperture.

17. The beam shaping assembly for neutron capture therapy according to claim 16, wherein a gap channel is provided between the moderator and the reflector to increase the epithermal neutron flux.

18. The beam shaping assembly for neutron capture therapy according to claim 17, wherein the first replacement member is mounted into the beam shaping assembly, the first replacement member comprises a first end, a second end and an inner surface extending form the first end to the second end, the first aperture is disposed on the first end flush with or protrudes from the beam outlet, the second end is adjacent to the gap channel, and the inner surface of the first replacement member is communicated with the gap channel.

\* \* \* \* \*